United States Patent
Yoshitake et al.

(10) Patent No.: US 10,335,304 B2
(45) Date of Patent: Jul. 2, 2019

(54) PRESSING TOOL FOR PELVIC FLOOR MUSCLE GROUP

(71) Applicant: Rika Takagi, D'Leedon (SG)

(72) Inventors: Hisayoshi Yoshitake, Aichi (JP); Satoko Soejima, Tokyo (JP); Haruyo Tani, Tokyo (JP); Naomi Watanabe, Tokyo (JP)

(73) Assignee: RIKA TAKAGI, D'Leedon (SG)

( * ) Notice: Subject to any disclaimer, the term of this patent is extended or adjusted under 35 U.S.C. 154(b) by 0 days.

(21) Appl. No.: 14/433,563

(22) PCT Filed: Dec. 11, 2014

(86) PCT No.: PCT/JP2014/082824
§ 371 (c)(1),
(2) Date: Apr. 3, 2015

(87) PCT Pub. No.: WO2015/093386
PCT Pub. Date: Jun. 25, 2015

(65) Prior Publication Data
US 2016/0278958 A1   Sep. 29, 2016

(30) Foreign Application Priority Data
Dec. 16, 2013 (JP) ................. 2013-259170

(51) Int. Cl.
*A61G 15/00* (2006.01)
*A61F 5/01* (2006.01)
(Continued)

(52) U.S. Cl.
CPC .............. *A61F 5/01* (2013.01); *A61F 6/08* (2013.01); *A61H 1/006* (2013.01); *A61H 7/001* (2013.01);
(Continued)

(58) Field of Classification Search
CPC ...... A61F 5/01; A61F 6/08; A61F 2015/0014; A61F 2201/0134; A61F 2201/0157;
(Continued)

(56) References Cited

U.S. PATENT DOCUMENTS 5,531,226 A * 7/1996 Harris ................. A61H 19/30
                                                    600/587
5,545,199 A * 8/1996 Hudson ................ A47G 9/1036
                                                    5/421

(Continued)

FOREIGN PATENT DOCUMENTS

JP   10-313970 A   12/1998
JP   10-337319 A   12/1998
(Continued)

OTHER PUBLICATIONS

JP201320217A—English Translation.*
(Continued)

*Primary Examiner* — Victoria J Hicks
(74) *Attorney, Agent, or Firm* — Muncy, Geissler, Olds & Lowe, P.C.

(57) ABSTRACT

With respect to a pressing tool main body 10B of a pressing tool for a pelvic floor muscle group 1B, a convex upper surface has a hardness of 10 to 20, which is a value of the International Rubber Hardness Degree (IRHD) complying with JIS K 6253, when the pressing tool main body 10B is in an initial state in which the pressing tool main body 10B is subject to no external force and is not squashed, and has a hardness of 25 to 35, which is a value of the International Rubber Hardness Degree (IRHD) complying with JIS K 6253, when the pressing tool main body 10B is subject to an external force, and a height from a seat surface to the convex upper surface becomes a half of the height from the seat surface to the convex upper surface in the initial state.

11 Claims, 6 Drawing Sheets

(51) Int. Cl.
*A61H 7/00* (2006.01)
*A61F 6/08* (2006.01)
*A61H 1/00* (2006.01)
*A61H 15/00* (2006.01)

(52) U.S. Cl.
CPC .......... *A61H 2015/0014* (2013.01); *A61H 2201/0134* (2013.01); *A61H 2201/0157* (2013.01); *A61H 2201/1284* (2013.01); *A61H 2201/1628* (2013.01); *A61H 2201/1695* (2013.01); *A61H 2203/0425* (2013.01); *A61H 2205/085* (2013.01)

(58) Field of Classification Search
CPC ..... A61F 2201/1628; A61F 2201/1695; A61H 2203/0425; A61H 2205/085; A61H 2205/086; A61H 2201/0138–0149; A61H 1/006; A61H 7/001; A61H 19/00; A61H 19/30; A61H 19/32; A61H 19/34; A61H 39/00; A61H 39/04; A63B 21/00189; A63B 21/0028; A63B 21/4039; A63B 23/16; A63B 23/20; A63B 26/00; A61G 5/1043; A61G 2005/1045; Y10S 5/948; Y10S 5/953; A47G 9/1036; A47G 9/1081; B62J 1/18; B62J 1/20; B62J 1/22; B62J 1/24; B62J 1/26
USPC ............. 601/24, 134, 136; 600/30; 128/845; 5/653, 652; 607/96, 98, 99, 109, 110, 607/114
See application file for complete search history.

(56) References Cited

U.S. PATENT DOCUMENTS

| | | | |
|---|---|---|---|
| 6,436,029 B1* | 8/2002 | Benderev | A61F 2/0009 128/885 |
| 7,473,214 B2* | 1/2009 | Schuurmans Stekhoven | A63B 23/20 482/142 |
| 2012/0329896 A1* | 12/2012 | Bloomfield | C08G 77/56 521/152 |
| 2014/0375089 A1* | 12/2014 | Qureshi | A47C 7/022 297/180.12 |
| 2015/0273270 A1* | 10/2015 | Brinkhaus | A63B 23/20 482/8 |

FOREIGN PATENT DOCUMENTS

| | | |
|---|---|---|
| JP | 2011-254878 A | 12/2011 |
| JP | 2013202174 A * | 10/2013 |
| WO | WO 2012-036188 A1 | 3/2012 |

OTHER PUBLICATIONS

Morgans (1999) "Understanding IRHD and Shore methods in rubber hardness testing". American Chemical Society Meeting; Sep. 21-24, 1999; Orlando, FL, USA.*

* cited by examiner

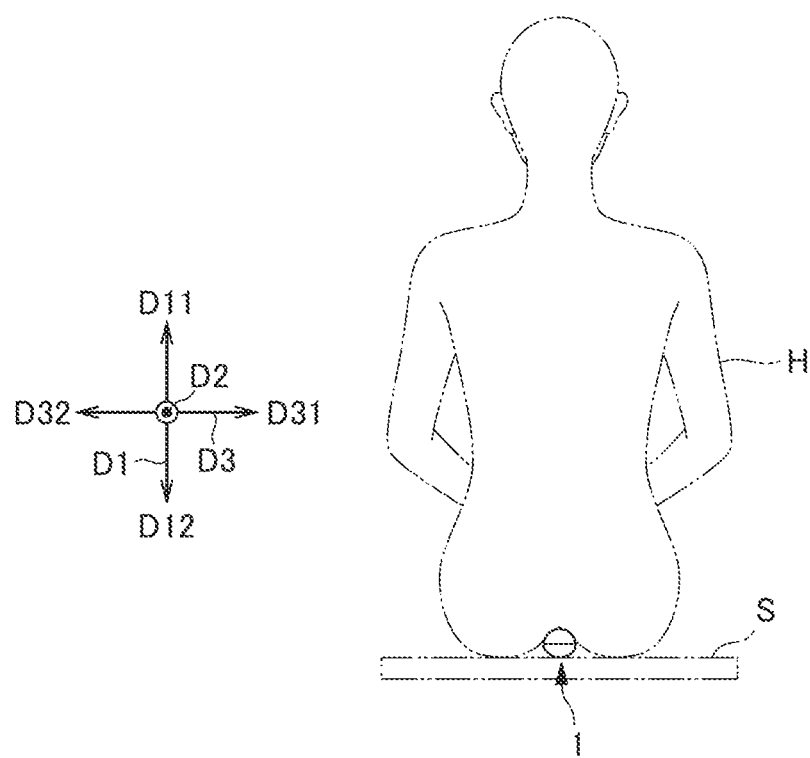

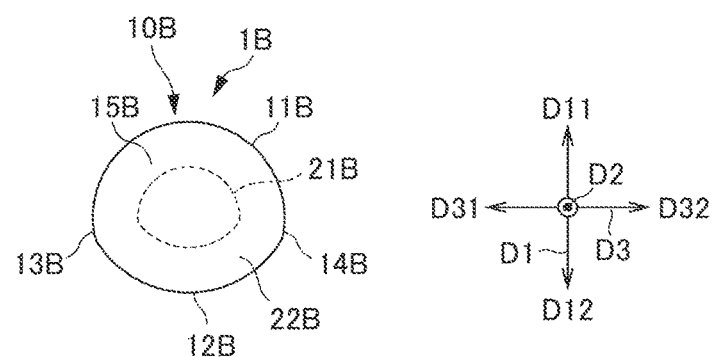
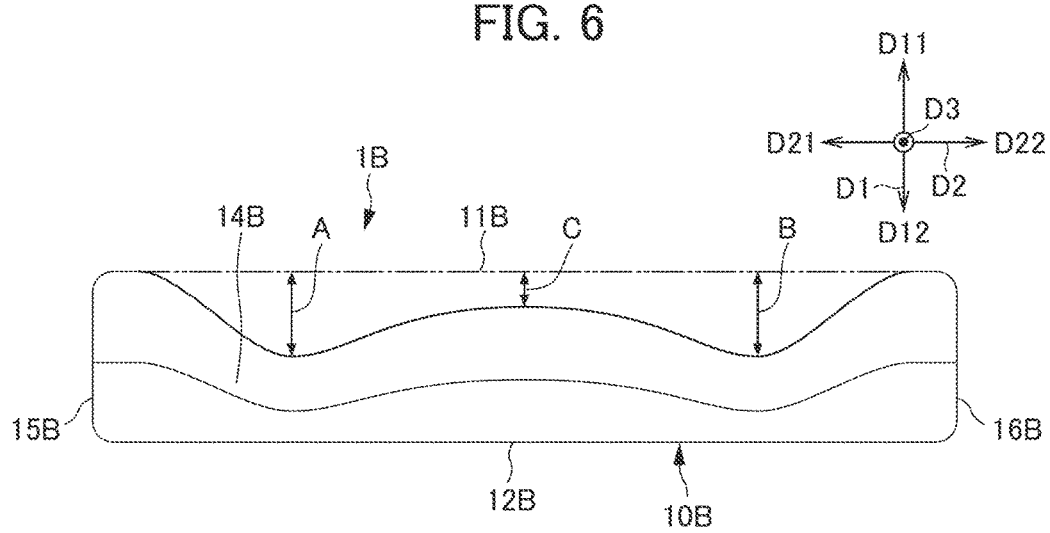

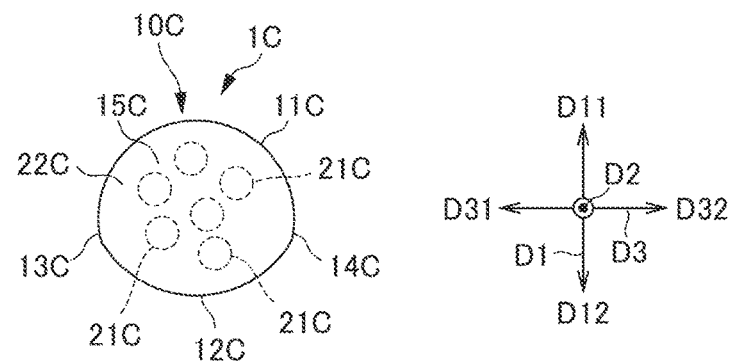
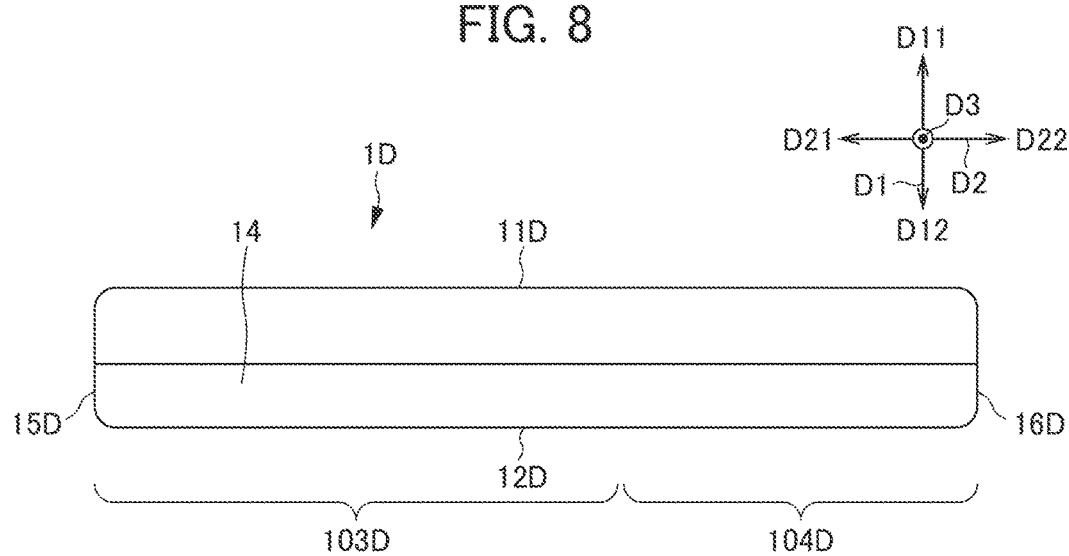

PRESSING TOOL FOR PELVIC FLOOR MUSCLE GROUP

TECHNICAL FIELD

The present invention relates to a pressing tool for a pelvic floor muscle group which presses a pelvic floor muscle group by making use of the weight of a human body.

BACKGROUND ART

Conventionally a corrective tool mounted on a seat surface to correct posture and the like is known of. The corrective tool includes an approximately halved cylindrical convex portion. The corrective tool is mounted on the seat surface to have a positional relationship in which the longitudinal direction of the convex portion is parallel to the right-left direction of the human body. The human body then sits on the seat surface and the corrective tool (refer to Patent Document 1).

Patent Document 1: Japanese Unexamined Patent Application, Publication No. H10-313970

DISCLOSURE OF THE INVENTION

Problems to be Solved by the Invention

The aforementioned corrective tool is designed for the correction of the posture of the human body from the outside of the human body but cannot improve posture by actively moving muscles inside the human body. In recent years, it is believed that active movement of muscles located inside the human body, such as the diaphragm, the transverse abdominal muscle, the multifidus muscle, and the erector spinae muscles will lead to improvement of posture. It is especially believed that these muscles are actively moved by pressing the pelvic floor muscle group.

However, pressing the pelvic floor muscle group means pressing the groin with fingers or the like. Young women especially may feel strong resistance in such pressing.

An object of the present invention is to provide a pressing tool for a pelvic floor muscle group which moderately presses a pelvic floor muscle group.

Means for Solving the Problems

The present invention relates to a pressing tool for a pelvic floor muscle group including a pressing tool main body having a length in a longitudinal direction at least as long as a length between a pubis and a coccyx of a human body and having a width in a width direction with respect to the longitudinal direction shorter than a length between an ischia, as a pair, of the human body, wherein a part of the pressing tool main body in the longitudinal, direction corresponding to the length between the pubis and the coccyx of the human body has a convex upper surface formed in a convex shape headed outward from the pressing tool main body, wherein the pressing tool for a pelvic floor muscle group is mounted to have a positional relationship in which the longitudinal direction corresponds to a front-back direction of the human body so that the convex upper surface may be located highest in the pressing tool main body and so that the longitudinal direction of the pressing tool main body may be along a seat surface, and the human body sits on the seat surface and mounts the convex upper surface to cause the convex upper surface to be opposed to the pubis and the coccyx and to press a pelvic floor muscle group, and wherein, as for the pressing tool main body, the convex upper surface has a hardness of 10 to 20, which is a value of the international Rubber Hardness Degree (IRHD) complying with JIS K 6253, when the pressing tool main body is in an initial state in which the pressing tool main body is subject to no external force and is not squashed, and has a hardness of 25 to 35, which is a value of the International Rubber Hardness Degree (IRHD) complying with JIS K 6253, when the pressing tool main body is subject to an external force, and a height from the seat surface to the convex upper surface becomes a half of the height from the seat surface to the convex upper surface in the initial state.

The present invention also relates to a pressing tool for a pelvic floor muscle group including a pressing tool main body having a length in a longitudinal direction at least as long as a length between a pubis and a coccyx of a human body and having a width in a width direction with respect to the longitudinal direction shorter than a length between an ischia, as a pair, of the human body, wherein a part of the pressing tool main body in the longitudinal direction corresponding to the length between the pubis and the coccyx of the human body has a convex upper surface formed in a convex shape protruding outward from the pressing tool main body, wherein the pressing tool for a pelvic floor muscle group is mounted to have a positional relationship in which the longitudinal direction corresponds to a front-back direction of the human body so that the convex upper surface may be located highest in the pressing tool main body and so that the longitudinal direction of the pressing tool main body may be along a seat surface, and the human body sits on the seat surface and mounts the convex upper surface to cause the convex upper surface to be opposed to the pubis and the coccyx and to press a pelvic floor muscle group, and wherein the pressing tool main body has a hardness of 1 or higher and 10 or lower or 20 or higher and 100 or lower, which is a value of the International Rubber Hardness Degree (IRHD) complying with JIS K 6253.

Also, the pressing tool main body preferably has a hard portion and a soft portion, and the soft portion preferably has a hardness of 1 or higher and 10 or lower, which is a value of the International Rubber Hardness Degree (IRHD) complying with JIS K 6253.

Also, the pressing tool main body preferably has a hard portion and a soft portion, and the hard portion preferably has a hardness of 20 or higher and 100 or lower, which is a value of the International Rubber Hardness Degree (IRHD) complying with JIS K 6253.

The present invention also relates to a pressing tool for a pelvic floor muscle group including a pressing tool main body having a length in a longitudinal direction at least as long as a length between a pubis and a coccyx of a human body and having a width in a width direction with respect to the longitudinal direction shorter than a length between an ischia, as a pair, of the human body, wherein a part of the pressing tool main body in the longitudinal direction corresponding to the length between the pubis and the coccyx of the human body has a convex upper surface formed in a convex shape protruding outward from the pressing tool main body, wherein the pressing tool for a pelvic floor muscle group is mounted to have a positional relationship in which the longitudinal direction corresponds to a front-back direction of the human body so that the convex upper surface may be located highest in the pressing tool main body and so that the longitudinal direction of the pressing tool main body may be along a seat surface, and the human body sits on the seat surface and mounts the convex upper surface to cause the convex upper surface to be opposed to the pubis and the coccyx and to press a pelvic floor muscle group, wherein a squashing amount of the pressing tool main body at a part of the convex upper surface opposed to the pubis in a direction approaching to the seat surface, derived by a position of the convex upper surface when the pressing tool main body is squashed by a weight of the human body relative to a position of the convex upper surface in an initial state, in which the pressing tool main body is subject to no external force and is not squashed, is referred to as A, wherein a squashing amount of the pressing tool main body at a part of the convex upper surface opposed to the coccyx in the direction approaching to the seat surface, derived by a position of the convex upper surface when the pressing tool main body is squashed by the weight of the human body relative to a position of the convex upper surface in the initial state, in which the pressing tool main body is subject to no external force and is not squashed, is referred to as B, wherein a squashing amount of the pressing tool main body at a part of the convex upper surface opposed to the pelvic floor muscle group between the pubis and the coccyx in the direction approaching to the seat surface, derived by a position of the convex upper surface when the pressing tool main body is squashed by the weight of the human body relative to a position of the convex upper surface in the initial state, in which the pressing tool main body is subject to no external force and is not squashed, is referred to as C, and wherein, at this time, $1.5 \leq A/C \leq 10$ and $1.4 \leq B/C \leq 9$ are established.

Also, the pressing tool for a pelvic floor muscle group preferably includes a pressing tool main body position confirming portion connected with an end of the pressing tool main body in the longitudinal direction of the pressing tool main body.

Also, an entire length of the pressing tool for a pelvic floor muscle group including the pressing tool main body and the pressing tool main body position confirming portion in the longitudinal direction of the pressing tool main body is preferably 300 mm or longer.

Also, the pressing tool for a pelvic floor muscle group preferably includes a lower surface having a positional relationship of being opposed to the convex upper surface, and a maximum distance between the convex upper surface and the lower surface is preferably 60 mm to 120 mm.

Effects of the Invention

According to the present invention, it is possible to provide a pressing tool for a pelvic floor muscle group which moderately presses a pelvic floor muscle group.

BRIEF DESCRIPTION OF THE DRAWINGS

FIG. 1(a) is a front view illustrating the pressing tool for a pelvic floor muscle group according to the first embodiment.

FIG. 1(b) is a plan view illustrating the pressing tool for a pelvic floor muscle group according to the first embodiment.

FIG. 1(c) is a right side view illustrating the pressing tool for a pelvic floor muscle group according to the first embodiment.

FIG. 2 is a rear view illustrating a state in which a pelvic floor muscle group of a human body is being pressed by the pressing tool for a pelvic floor muscle group according to the first embodiment.

FIG. 3(a) is a front view illustrating the pressing tool for a pelvic floor muscle group according to the second embodiment.

FIG. 3(b) is a plan view illustrating the pressing tool for a pelvic floor muscle group according to the second embodiment.

FIG. 3(c) is a right side view illustrating the pressing tool for a pelvic floor muscle group according to the second embodiment.

FIG. 5 is a front view illustrating a pressing tool for a pelvic floor muscle group according to a third embodiment.

FIG. 6 is a right side view illustrating a state in which the pressing tool for a pelvic floor muscle group according to the third embodiment is being used and deformed.

FIG. 7 is a front view illustrating a pressing tool for a pelvic floor muscle group according to a fourth embodiment.

FIG. 8 is a right side view illustrating a pressing tool for a pelvic floor muscle group according to a fifth embodiment.

PREFERRED MODE FOR CARRYING OUT THE INVENTION

Figure 1A:
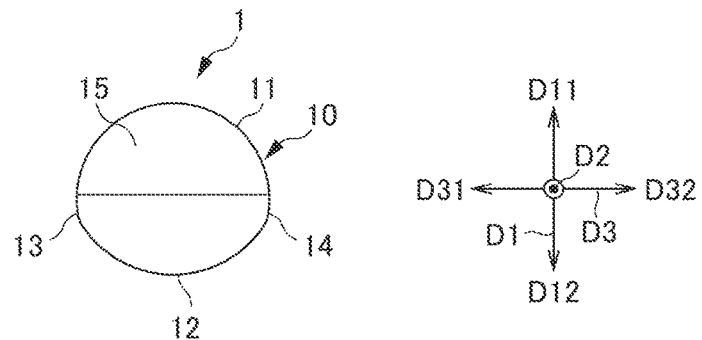
FIGS. 1(a) to 1(c) illustrate a pressing tool for a pelvic floor muscle group according to a first embodiment.
Figure 1B:
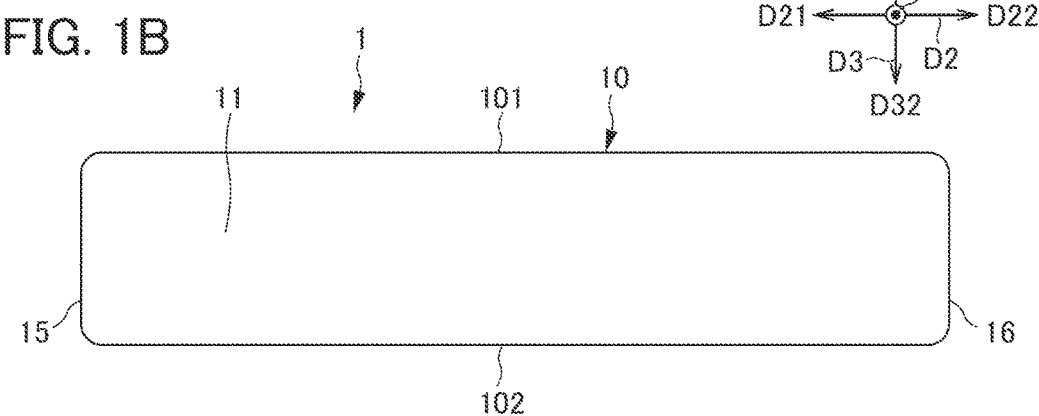
Figure 1C:
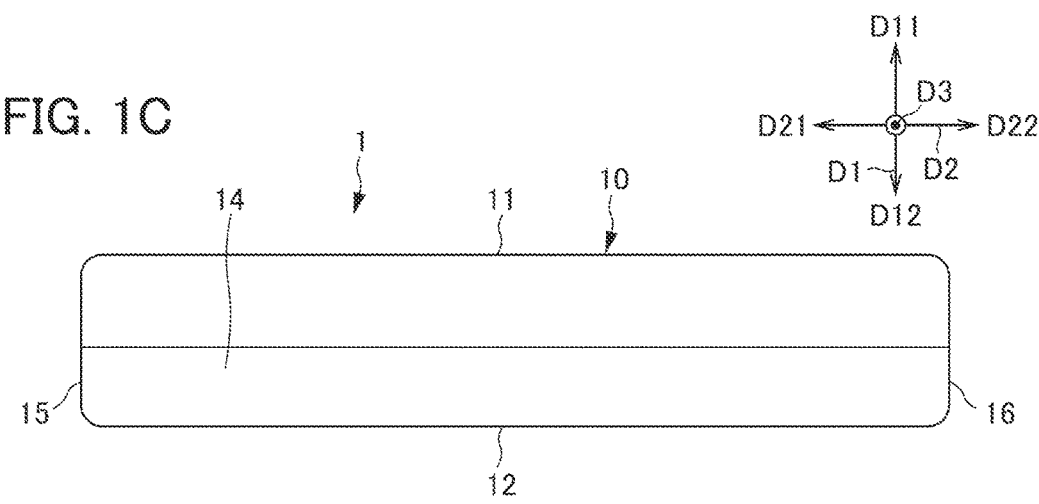
Figure 3A:
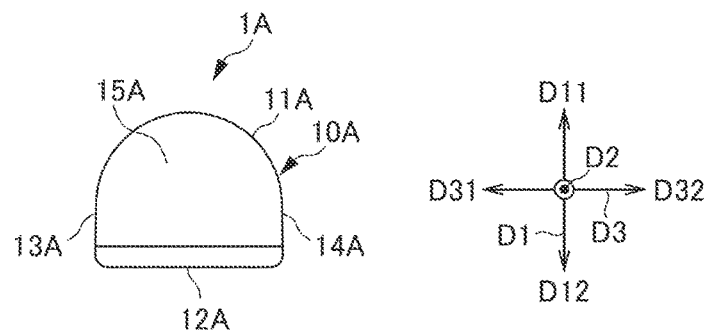
FIGS. 3(a) to 3(c) illustrate a pressing tool for a pelvic floor muscle group according to a second embodiment.
Figure 3B:
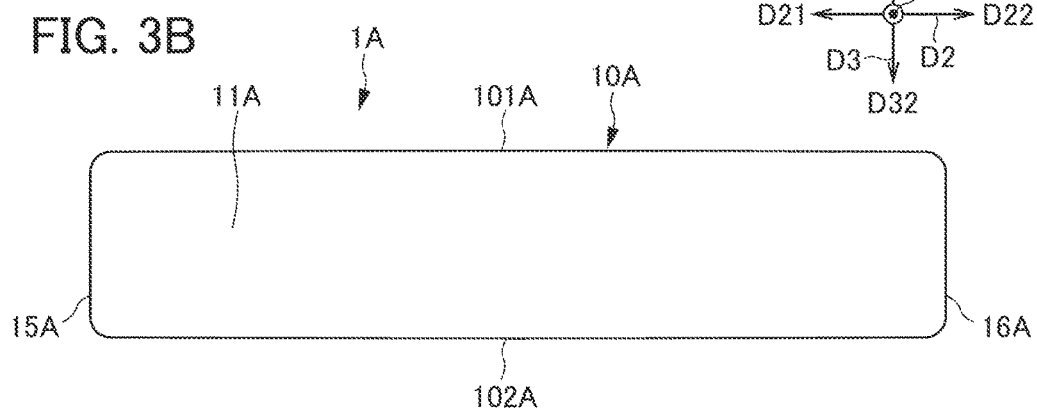
Figure 3C:
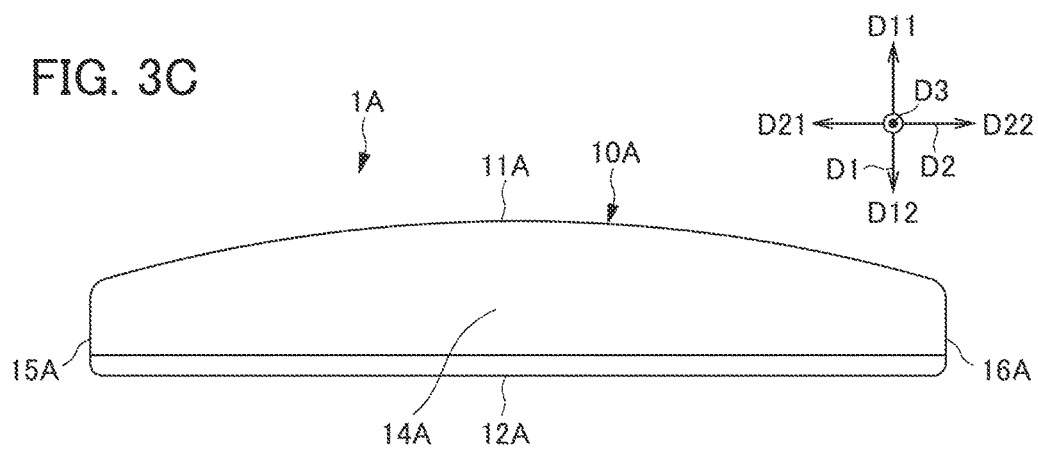
Figure 4:
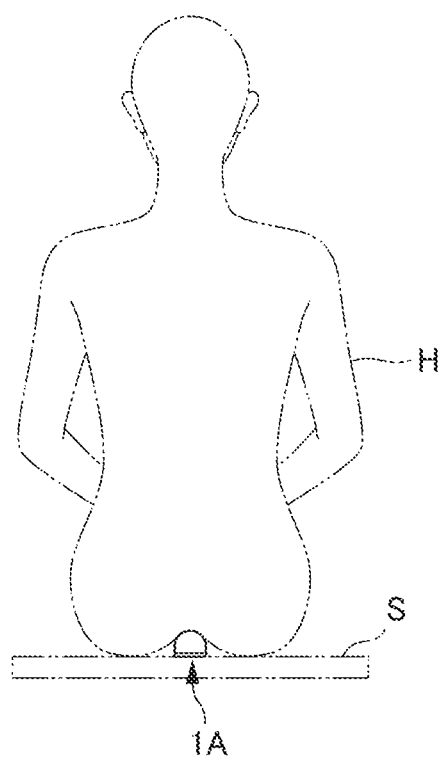
FIG. 4 is a rear view illustrating a state in which the pelvic floor muscle group of the human body is being pressed by the pressing tool for a pelvic floor muscle group according to the second embodiment.

Hereinafter, a pressing tool for a pelvic floor muscle group according to a first embodiment of the present invention will be described with reference to the drawings. FIGS. 1(a) to 1(c) illustrate the pressing tool for a pelvic floor muscle group according to the first embodiment, and FIG. 1(a) is a front view illustrating the pressing tool for a pelvic floor muscle group according to the first embodiment. FIG. 1(b) is a plan view illustrating the pressing tool for a pelvic floor muscle group according to the first embodiment. FIG. 1(c) is a right side view illustrating the pressing tool for a pelvic floor muscle group according to the first embodiment. FIG. 2 is a rear view illustrating a state in which a pelvic floor muscle group of a human body is being pressed by the pressing tool, for a pelvic floor muscle group according to the first embodiment. FIGS. 3(a) to 3(c) illustrate a pressing tool for a pelvic floor muscle group according to a second embodiment, and FIG. 3(a) is a front view illustrating the pressing tool for a pelvic floor muscle group according to the second embodiment. FIG. 3(b) is a plan view illustrating the pressing tool for a pelvic floor muscle group according to the second embodiment. FIG. 3(c) is a right side view illustrating the pressing tool for a pelvic floor muscle group according to the second embodiment. FIG. 4 is a rear view illustrating a state in which the pelvic floor muscle group of the human body is being pressed by the pressing tool for a pelvic floor muscle group according to the second embodiment.

Here, for convenience of description, the direction from a convex lower surface 12 toward a convex upper surface 11 of a pressing tool for a pelvic floor muscle group 1 to be described later is defined as an upper direction D11, the opposite direction thereof is defined as a lower direction D12, and these directions are defined as an up-down direction D1. Also, the direction perpendicular to the up-down direction D1 from the front side toward the back side of the drawing sheet of FIG. 2 is defined as a front direction D21, the opposite direction thereof is defined as a back direction D22, and these directions are defined as a front-back direction D2. Also, the direction which is perpendicular to the up-down direction D1 and which is the right direction in FIG. 2 is defined as a left direction D31, the opposite direction thereof is defined as a right direction D32, and these directions are defined as a right-left direction D3.

As illustrated in FIGS. 1(a) to 2, the pressing tool for a pelvic floor muscle group 1 includes a pressing tool main body 10 having the convex upper surface 11, the convex lower surface 12, a left connecting curved surface 13, a right connecting curved surface 14, a front end surface 15, and a back end surface 16.

The convex upper surface 11 is curved, outward in the upper direction D11 from one end to the other end of the width with respect to the front-back direction D2 serving as the longitudinal direction of the pressing tool for a pelvic floor muscle group 1, that is, from a left end 101 to a right end 102 of the pressing tool for a pelvic floor muscle group 1. The shape of the curve is uniform from the front end surface 15 to the back end surface 16 of the pressing tool for a pelvic floor muscle group 1. In other words, the part of the pressing tool for a pelvic floor muscle group 1 which is the entire part in the longitudinal direction of the pressing tool for a pelvic floor muscle group 1 corresponding to the length between the pubis and the coccyx of the human body H (refer to FIG. 2) has a convex upper surface 11. The convex upper surface 11 of the pressing tool or a pelvic floor muscle group 1 is formed approximately in a semicircular shape having a radius of 22.5 mm as seen from the front surface as illustrated in FIG. 1(a).

The convex lower surface 12 is located on the lower direction D12 side of the convex upper surface 11 and has the positional relationship of being opposed to the convex upper surface 11. The convex lower surface 12 is curved outward to a lower side from one end to the other end of the width with respect to the front-back direction D2 serving as the longitudinal direction of the pressing tool for a pelvic floor muscle group 1, that is, from the left end 101 to the right end 102 of the pressing tool for a pelvic floor muscle group 1. The shape of the curve is uniform from the front end surface 15 to the back end surface 16 of the pressing tool for a pelvic floor muscle group 1. Hence, the convex lower surface 12 of the pressing tool for a pelvic floor muscle group 1 is formed in an arc having a radius of 30 mm as seen from the front surface as illustrated in FIG. 1(a).

The left end edge of the convex upper surface 11 and the left end edge of the convex lower surface 12 are connected by the left connecting curved surface 13 curved in the left direction D31. Similarly, the right end edge of the convex upper surface 11 and the right end edge of the convex lower surface 12 are connected by the right, connecting curved surface 14 curved in the left direction D31. Both the left connecting curved surface 13 and the right connecting curved surface 14 each have a constant width of 4.5 mm in the up-down direction D1 from the front end surface 15 to the back end surface 16 of the pressing tool for a pelvic floor muscle group 1. Both the left connecting curved surface 13 and the right connecting curved surface 14 are each formed in an arc having a radius of 8 mm as seen from the front surface as illustrated in FIG. 1(a).

The front end surface 15 and the back end surface 16 have a mutually parallel positional relationship. The front end surface 15 and the back end surface 16 are also perpendicular to the front-back direction D2. Each connecting part of the front end surface 15 or the back end surface 16 and the convex upper surface 11, the convex lower surface 12, the left connecting curved surface 13, or the right connecting curved surface 14 is formed in a round chamfered shape having a radius of 5 mm or so.

The length between the front end surface 15 and the back end surface 16, that is, the length (the entire length) in the longitudinal direction of the pressing tool for a pelvic floor muscle group 1, is 207 mm. Accordingly, the pressing tool for a pelvic floor muscle group 1 is longer in length (entire length) than the length between the pubis and the coccyx of the human body H in the longitudinal direction. Also, the width in the right-left direction D3 is 45 mm. Accordingly, the pressing tool for a pelvic floor muscle group 1 is shorter in width than the length between the ischia, as a pair, of the human body H in the right-left direction D3 serving as the width direction. Also, the maximum distance between the convex upper surface 11 and the convex lower surface 12 of the pressing tool for a pelvic floor muscle group 1, that is, the distance from the upper end to the lower end of the pressing tool for a pelvic floor muscle group 1, is preferably from 30 mm to 60 mm. In the first embodiment, the distance from the upper end to the lower end of the pressing tool for a pelvic floor muscle group 1 is 50 mm. In a case in which the distance is less than 30 mm, the amount of pressing toward the pelvic floor muscle group is insufficient. Conversely, in a case in which the distance is more than 60 mm, the human body H feels pain in the part around the pubis and the part around the coccyx.

The pressing tool for a pelvic floor muscle group 1 is made of a urethane resin. Also, the pressing tool for a pelvic floor muscle group 1 has a hardness of 10 to 20, which is a value of the International Rubber Hardness Degree (IRHD) complying with JIS K 6253. The hardness of the pressing tool for a pelvic floor muscle group 1 according to the first embodiment is 12. In a case when it is less than 10, the pressing tool for a pelvic floor muscle group 1 is so hard that the human body H feels pain in the part around the pubis and a part around the coccyx. Conversely, in a case when it is more than 20, the pressing tool for a pelvic floor muscle group 1 is so soft that the amount of pressing toward the pelvic floor muscle group is insufficient.

This hardness value is measured and obtained by bringing a "JIS" TECLOCK Durometer (manufactured by TECLOCK Corporation) into contact with the part of the convex upper surface 11 corresponding to the center position of the pressing tool for a pelvic floor muscle group 1 in the front-back direction D2 and corresponding to the center position in the right-left direction D3 so that the measuring instrument may have the positional relationship of being perpendicular to the convex upper surface 11.

The pressing tool for a pelvic floor muscle group 1 configured as above is used in the following manner. First, as illustrated in FIG. 2, the pressing tool for a pelvic floor muscle group 1 is mounted on the seat surface S of a chair or the like to have the positional relationship in which the longitudinal direction thereof corresponds to the front-back direction D2 of the human body H, that is, to have the positional relationship in which the front direction D21 and the back direction D22 of the human body H respectively correspond to the front direction D21 and the back direction D22 of the pressing tool for a pelvic floor muscle group 1, so that the convex upper surface 11 may be located highest in the pressing tool main body 10 and so that the longitudinal direction of the pressing tool main body 10 may be along the seat surface S. Subsequently, the human body H sits on the seat surface S and mounts the convex upper surface 11 of the pressing tool for a pelvic floor muscle group 1 to have the positional relationship in which the convex upper surface 11 is opposed to the pubis and the coccyx of the human body H.

At this time, due to a weight of the upper body of the human body H sitting on the seat surface S and the pressing tool for a pelvic floor muscle group 1, the pelvic floor muscle group presses the pressing tool for a pelvic floor muscle group 1. At the same time, the gluteal and the thigh muscles press the seat surface S.

In response, the pelvic floor muscle group receives a reaction force from the pressing tool for a pelvic floor muscle group 1, and at the same time, the gluteal and the thigh muscles receive a reaction force from the seat surface S. The human body H attempts to adjust its posture to prevent the part around the pubis and the part around the coccyx from being stimulated as much as possible and moves not only the gluteal and the thigh muscles but also the pelvic floor muscle group pressed by the convex upper surface 11 of the pressing tool for a pelvic floor muscle group 1 and the so-called inner muscles (the diaphragm, the transverse abdominal muscle, the multifidus muscle, the erector spinae muscle, and the like) around it. Although it is difficult to move these muscles unless one touches them with the fingers or the like and gains consciousness of them, one can gain consciousness of them and move them by pressing the pelvic floor muscle group with the pressing tool for a pelvic floor muscle group 1.

That is, the pressing tool for a pelvic floor muscle group 1 has a length in the longitudinal direction (front-back direction D2) as long as the length between the pubis and the coccyx of the human body H and has a width in the width direction (right-left direction D1) with respect to the longitudinal direction shorter than the length between the ischia, as a pair, of the human body H, and the entire part in the longitudinal direction corresponding to the length between the pubis and the coccyx of the human body H has the convex upper surface 11 curved outward from one end to the other end of the width with respect to the longitudinal direction. Accordingly, the pelvic floor muscle group receives the reaction force from the convex upper surface 11 of the pressing tool for a pelvic floor muscle group 1, and the human body H can adjust its posture to prevent the pubis and the coccyx from being stimulated and move the pelvic floor muscle group and the so-called inner muscles (the diaphragm, the transverse abdominal muscle, the multifidus muscle, and the erector spinae muscle) around it. This not only brings about good posture but also prevents urinary incontinence and enables the reduction of the waist dimension.

Next, a pressing tool for a pelvic floor muscle group 1A according to a second embodiment of the present invention will be described with reference to FIGS. 3(a) to 4. The external shape and the hardness of the pressing tool for a pelvic floor muscle group 1A according to the second embodiment differ from those of the pressing tool for a pelvic floor muscle group 1 according to the first embodiment. The other parts are equal to those of the pressing tool for a pelvic floor muscle group 1 according to the first embodiment, and the description thereof is thus omitted.

The pressing tool for a pelvic floor muscle group 1A includes a pressing tool main body 10A having a convex upper surface 11A, a lower surface 12A, a left connecting flat surface 13A, a right connecting flat surface 14A, a front end surface 15A, and a back end surface 16A.

The convex upper surface 11A is curved outward to the upper direction D11 from one end to the other end of the width with respect to the front-back direction D2 serving as the longitudinal direction of the pressing tool for a pelvic floor muscle group 1A, that is, from a left end 101A to a right end 102A of the pressing tool for a pelvic floor muscle group 1A. The convex upper surface 11A is also curved outward (upper direction D11) from the one end portion to the other end portion in the longitudinal direction, that is, from the front end surface 15A to the back end surface 16A in the figures. Accordingly, the center portion in the right-left direction D3 of the pressing tool for a pelvic floor muscle group 1A, which is also the center portion in the front-back direction D2, projects the most to the upper direction D11.

In other words, the part of the pressing tool for a pelvic floor muscle group 1A, which is the entire part in the longitudinal direction of the pressing tool for a pelvic floor muscle group 1A corresponding to the length between the pubis and the coccyx of the human body H, has the convex upper surface 11A formed in such a shape. The pressing tool for a pelvic floor muscle group 1A is formed approximately in a semicircular shape having a radius of 22.5 mm as seen from the front surface as illustrated in FIG. 3.

The lower surface 12A has the positional relationship of being opposed to the convex upper surface 11A. The lower surface 12A is constituted of a planar surface.

The left end edge of the convex upper surface 11A and the left end edge of the lower surface 12A are connected by the planar left connecting flat surface 13A. Similarly, the right end edge of the convex upper surface 11A and the right end edge of the lower surface 12A are connected by the planar right connecting flat surface 14A. The virtual extending flat surface of the left connecting flat surface 13A and the virtual extending flat surface of the right connecting flat surface 14A have the positional relationship of intersecting at an angle of 2° at a position located further on the side of the lower direction D12 than the lower surface 12A.

The front end surface 15A and the back end surface 16A have a mutually parallel positional relationship. The front end surface 15A and the back end surface 16A are also perpendicular to the front-back direction D2. Each connecting part of the front end surface 15A or the back end surface 16A and the convex upper surface 11A, the lower surface 12A, the left connecting flat surface 13A, or the right connecting flat surface 14A is formed in a chamfered shape having a radius of 5 mm or so.

The length between the front end surface 15A and the back end surface 16A, that is, the length in the longitudinal direction of the pressing tool for a pelvic floor muscle group 1A, is preferably 180 mm or longer, and is 207 mm in the pressing tool for a pelvic floor muscle group 1A according to the second embodiment. Accordingly, the pressing tool for a pelvic floor muscle group 1A is longer in length (entire length) than the length between the pubis and the coccyx of the human body H in the longitudinal direction. Also, the width in the right-left direction D3 is 45 mm. Accordingly, the pressing tool for a pelvic floor muscle group 1A is shorter in width than the length between the ischia, as a pair, of the human body H in the right-left direction D3 serving as the width direction. Also, the maximum distance between the convex upper surface 11A and the lower surface 12A of the pressing tool for a pelvic floor muscle group 1A, that is, the distance from the upper end to the lower end of the pressing tool for a pelvic floor muscle group 1A, is preferably from 30 mm to 60 mm. In the second embodiment, the distance from the upper end to the lower end of the pressing tool for a pelvic floor muscle group 1A is 50 mm. In a case in which the distance is less than 30 mm, the amount of pressing toward the pelvic floor muscle group is insufficient. Conversely, in a case in which the distance is more than 60 mm, the human body H feels pain in the part around the pubis and the part around the coccyx.

Also, the pressing tool for a pelvic floor muscle group 1A has a hardness of 10 to 20, which is a value of the International Rubber Hardness Degree (IRHD) complying with JIS K 6253. The hardness of the pressing tool for a pelvic floor muscle group 1A according to the second embodiment is 14. In the case when this figure is less than 10, the pressing tool for a pelvic floor muscle group 1A is so hard that the human body H feels pain in the part around the pubis and the part around the coccyx. Conversely, in the case when this figure is more than 20, the pressing tool for a pelvic floor muscle group 1A is so soft that the amount of pressing toward the pelvic floor muscle group is insufficient. The method for measuring the hardness is similar to the method for measuring the hardness in the first embodiment.

The pressing tool for a pelvic floor muscle group 1A configured as above is used in a similar manner to that for the pressing tool for a pelvic floor muscle group 1 according to the first embodiment. At this time, since the convex upper surface 11A is curved outward (upward) from one end (front end surface 15A) to the other end (back end surface 16A) in the longitudinal direction, the part around the pubis and the part around the coccyx of the human body H can be stimulated less when the pelvic floor muscle group receives a reaction force from the pressing tool for a pelvic floor muscle group 1A.

Accordingly, even in the case in which a user is stimulated and feels pain when he/she uses the pressing tool for a pelvic floor muscle group 1 according to the first embodiment, he/she can press his/her pelvic floor muscle group with comfort without feeling pain when he/she uses the pressing tool for a pelvic floor muscle group 1 according to the second embodiment.

Next, a test was conducted to confirm the effect of the present invention by changing the maximum distance between the convex upper surface 11A and the lower surface 12A of the pressing tool for a pelvic floor muscle group. In the test, the pressing tool for a pelvic floor muscle group 1A according to the second embodiment was called Invented Product 2. Also products having the maximum distances in the up-down direction D1 of 20 mm, 25 mm, 35 mm, 55 mm, 65 mm, and 70 mm and each having the other configurations that are equal to those of the pressing tool for a pelvic floor muscle group 1A according to the second embodiment were called Comparative Product 1, Comparative Product 2, Invented Product 1, Invented Product 3, Comparative Product 3, and Comparative Product 4, respectively. Fifty examinees used the pressing tools for the pelvic floor muscle group to examine whether or not each of them felt pain in the part around the pubis and the part around the coccyx and the degree of pressing on the pelvic floor muscle group.

Specifically, the number of examinees who each felt severe pain in the part around the pubis and the part around the coccyx out of the fifty examinees was counted as the number of "Pain" examinees. Also, the number of examinees who each felt that the degree of pressing on the pelvic floor muscle group was sufficient out of the fifty examinees was counted as the number of "Sufficient Pressing" examinees. The test result is shown in Table 1 below.

TABLE 1

| | Comparative Product 1 | Comparative Product 2 | Invented Product 1 | Invented Product 2 | Invented Product 3 | Comparative Product 3 | Comparative Product 4 |
|---|---|---|---|---|---|---|---|
| Pain | 5 People | 6 People | 7 People | 10 People | 11 People | 43 People | 49 People |
| Sufficient Pressing | 8 People | 10 People | 40 People | 45 People | 47 People | 48 People | 50 People |

As shown in Table 1, while the number of examinees who felt severe pain is small in Invented Product 1, Invented Product 2, and Invented Product 3, most of the examinees felt severe pain in Comparative Product 3 and Comparative Product 4. On the other hand, while many examinees felt that the degree of pressing was sufficient in Invented Product 1, Invented Product 2, and invented Product 3, most of the examinees felt that the degree of pressing was insufficient in Comparative Product 1 and Comparative Product 2. It is apparent from this result that the Invented Products which have the maximum distance between the convex upper surface and the lower surface of from 30 mm to 60 mm do not make the examinees feel severe pain and press the pelvic floor muscle group in a sufficient degree.

Also, a test was conducted to confirm the effect of the present invention by changing the hardness of the pressing tool for a pelvic floor muscle group. In the test, the pressing tool for a pelvic floor muscle group 1A according to the second embodiment was called Invented Product 2. Also products having the hardness (IRHD) values of 26, 21, 20, 11, 7, and 9 and each having other configurations equal to those of the pressing tool for a pelvic floor muscle group 1A according to the second embodiment were called Comparative Product 1, Comparative Product 2, Invented Product 1, Invented Product 3, Comparative Product 3, and Comparative Product 4, respectively. Fifty examinees used the pressing tools for the pelvic floor muscle group to examine whether or not each of them felt pain in the part around the pubis and the part around the coccyx and the degree of pressing on the pelvic floor muscle group.

Specifically, the number of examinees who each felt severe pain in the part around the pubis and the part around the coccyx out of the fifty examinees was counted as the number of "Pain" examinees. Also, the number of examinees who each felt that the degree of pressing on the pelvic floor muscle group was sufficient out of the fifty examinees was counted as the number of "Sufficient Pressing" examinees. The test result is shown in Table 2 below.

TABLE 2

|  | Comparative Product 1 | Comparative Product 2 | Invented Product 1 | Invented Product 2 | Invented Product 3 | Comparative Product 3 | Comparative Product 4 |
|---|---|---|---|---|---|---|---|
| Pain | 0 People | 3 People | 6 People | 10 People | 12 People | 43 People | 49 People |
| Sufficient Pressing | 5 People | 6 People | 38 People | 45 People | 47 People | 49 People | 49 People |

As shown in Table 1, while the number of examinees who felt severe pain is small in Invented Product 1, invented Product 2, and Invented Product 3, most of the examinees felt severe pain in Comparative Product 3 and Comparative Product 4. On the other hand, as shown in Table 1, while many examinees felt that the degree of pressing was sufficient in Invented Product 1, Invented Product 2, and Invented Product 3, most of the examinees felt that the degree of pressing was insufficient in Comparative Product 1 and Comparative Product 2. It is apparent from this result that Invented Products which have a hardness of from 10 to 20, which is a value of the International Rubber Hardness Degree (IRHD) complying with JIS K 6253, do not make the examinees feel severe pain and press the pelvic floor muscle group to a sufficient degree.

Also, a hundred examinees used the pressing tools for the pelvic floor muscle group 1A according to the second embodiment for seven days, twice a day, for about two minutes per use, to examine how effective the tools were for urinary incontinence. The number of examination items was six, and the examinees answered the six multiple-choice items. Specifically, the examination items are as follows.

Item 1. How often does urinary incontinence occur?
Item 2. How much do you think urine leaks?
Item 3. Overall, how much is your daily life impaired due to urinary incontinence?
Item 4. In what situations does urinary incontinence occur?
Item 5. Please tell us your frequency of urination.
Item 6. Do you sleep well at night.?

With respect to Item 1, each examinee chose one from among the options of "(A1) Not at all," "(B1) About once or less a week," "(C1) Twice to three times a week," "(D1) About once a day," "(E1) Several times a day," and "(F1) All the time" before and after using the pressing tool for a pelvic floor muscle group 1A, and the number of examinees who selected each option was obtained.

With respect to Item 2, each examinee chose one from among the options of "(A2) It does not," "(B2) A small amount," "(C2) A medium amount," and "(D2) A large amount" before and after using the pressing tool for a pelvic floor muscle group 1A, and the number of examinees who selected each option was obtained.

With respect to Item 3, each examinee conducted a ten-grade evaluation consisting of 0 (Not impaired at all) to 10 (Extremely impaired) and chose one from among the options of "(A3) 0 to 3," "(B3) 4 to 7," and "(C3) 8 to 10" obtained by dividing the ten grades into three before and after using the pressing tool for a pelvic floor muscle group 1A, and the number of examinees who selected each option was obtained.

With respect to Item 4, each examinee chose one from among the options of "(A4) It does not, no urine leakage," "(B4) Leaks before I reach the toilet," "(C4) Leaks when I cough or sneeze," "(D4) Leaks while I am sleeping," "(E4) Leaks when I am moving my body or exercising," "(F4) Leaks when I finish urination and put on my clothes," "(G4) Leaks without knowing why," and "(H4) Leaks all the time" before and after using the pressing tool for a pelvic floor muscle group 1A, and the number of examinees who selected each option was obtained.

With respect to Item 5, each examinee gave the number of times of urination "(A5) During daytime (during waking hours)" and "(B5) During nighttime (while in bed)," before and after using the pressing tool for a pelvic floor muscle group 1A, and the average number was calculated.

With respect to Item 6, each examinee chose one from among the options of "(A6) Yes, I do," "(B6) I sleep reasonably well," "(C6) I do not sleep well," and "(D6) I do not sleep at all" before and after using the pressing tool for a pelvic floor muscle group 1A, and the number of examinees who selected each option was obtained.

The test results for the respective items are shown in Tables 3 to 8 below.

TABLE 3

| Item 1 | A1 | B1 | C1 | D1 | E1 | F1 |
|---|---|---|---|---|---|---|
| Before Use | 67 | 20 | 8 | 3 | 1 | 1 |
| After Use | 90 | 6 | 3 | 1 | 0 | 0 |

TABLE 4

| Item 2 | A2 | B2 | C2 | D2 |
|---|---|---|---|---|
| Before Use | 67 | 28 | 4 | 1 |
| After Use | 90 | 9 | 1 | 0 |

TABLE 5

| Item 3 | A3 | B3 | C3 |
|---|---|---|---|
| Before Use | 87 | 11 | 2 |
| After Use | 95 | 4 | 1 |

TABLE 6

| Item 4 | A4 | B4 | C4 | D4 | E4 | F4 | G4 | H4 |
|---|---|---|---|---|---|---|---|---|
| Before Use | 67 | 1 | 33 | 0 | 12 | 1 | 1 | 1 |
| After Use | 90 | 0 | 7 | 0 | 3 | 0 | 0 | 0 |

TABLE 7

| Item 5 | A5 | B5 |
|---|---|---|
| Before Use | 7 Times On Average | 3 Times On Average |
| After Use | 5 Times On Average | Once On Average |

TABLE 8

| Item 6 | A6 | B6 | C6 | D6 |
|---|---|---|---|---|
| Before Use | 46 | 27 | 19 | 8 |
| After Use | 63 | 29 | 7 | 1 |

As shown in Tables 3 to 8, the state of the urinary incontinence of the one hundred examinees is significantly improved. Specifically, as shown in Table 3, the frequency of urinary incontinence significantly decreases after use of the pressing tool for a pelvic floor muscle group 1A. Also, as shown in Table 4, the amount of urine that leaks decreases significantly after using the pressing tool for a pelvic floor muscle group 1A. Also, as shown in Table 5, the degree of impairment of their daily lives due to the urinary incontinence significantly decreases after using the pressing tool for a pelvic floor muscle group 1A.

Also, as shown in Table 6, although urinary incontinence occurred in various situations, urinary incontinence hardly occurs after using the pressing tool for a pelvic floor muscle group 1A.

Also, as shown in Table 7, the number of times of urination both during daytime and during nighttime decreases after using the pressing tool for a pelvic floor muscle group 1A. Also, as shown in Table 8, each examinee sleeps better after using the pressing tool for a pelvic floor muscle group 1A than before use. It is apparent from this result that urinary incontinence is significantly improved by using the pressing tool for a pelvic floor muscle group 1A regularly for a predetermined time.

Next, a pressing tool for a pelvic floor muscle group 1B according to a third embodiment of the present invention will be described with reference to FIGS. 5 and 6. The dimensions and the like of the pressing tool for a pelvic floor muscle group 1N according to the third embodiment partially differ from those of the pressing tool for a pelvic floor muscle group 1 according to the first embodiment. The other parts are equal to those of the pressing tool for a pelvic floor muscle group 1 according to the first embodiment, and descriptions thereof are thus omitted.

The convex upper surface 11B serving as the upper surface of the pressing tool for a pelvic floor muscle group 1B is formed approximately in a semicircular shape having a radius of 22.5 mm as seen from the front surface as illustrated in FIG. 5. Also, the convex lower surface 12B serving as the lower surface of the pressing tool for a pelvic floor muscle group 1 is formed in an arc having a radius of 30 mm as seen from the front surface as illustrated in FIG. 5. The distance from the upper end to the lower end of the pressing tool for a pelvic floor muscle group 1B, that is, the maximum distance between the convex upper surface 11A serving as the upper surface and the convex lower surface 12B serving as the lower surface, is 41 mm.

The pressing tool main body 10B of the pressing tool for a pelvic floor muscle group 1B has a hard portion 21B and a soft portion 22B both made of a urethane resin. The hard portion 21B constitutes the center portion of the pressing tool main body 10B and is located extending from the vicinity of one end portion to the vicinity of the other end portion in the longitudinal direction of the pressing tool main body 10B as illustrated in FIG. 5. The soft portion 22B is located so as to very thinly cover the entirety of the hard portion 21B. It is to be noted that the soft portion 22B is illustrated as being thick in FIG. 5 for convenience of description.

The hard portion 21B has only to have a hardness of 20 or higher and 100 or lower, which is a value of the international. Rubber Hardness Degree (IRHD) complying with JIS K 6253, more preferably has only to have a hardness of 20 or higher and 50 or lower, and has a hardness of 25 in the present embodiment. In a case in which the hardness of the hard portion 21B is less than 20, providing the hard portion 21B against the soft portion 22B, which is soft, will be meaningless, and pressing toward the pelvic floor muscle group will be insufficient. Also, in a case in which the hardness of the hard portion 21B exceeds 50, selectable materials for the soft portion 22B in relation to the hard portion 21B will be extremely few, which causes it to be difficult to form the pressing tool main body 10B that can achieve a moderate pressing feeling by combining the hard portion 21B with the soft portion 22B. Furthermore, in a case of more than 100, the hard portion 21B is so hard that it is difficult to obtain elasticity. The soft portion 22B has a hardness of 1 or higher and 10 or lower, which is a value of the international Rubber Hardness Degree (IRHD) complying with JIS K 6253, and has a hardness of 7 in the present embodiment. In a case in which the hardness of the soft portion 22E is less than 1, the soft portion 22B is so soft that elasticity is insufficient. Also, in a case in which the hardness of the soft portion 22B exceeds 10, selectable materials for the hard portion 21B in relation to the soft portion 22B will be extremely few, which causes it to be difficult to form the pressing tool main body 10B that can achieve a moderate pressing feeling by combining the hard portion 21B with the soft portion 22B.

These hardness values are measured and obtained by preparing measurement pieces each having a thickness of 10 mm made of the some materials as those for the hard portion 21B and the soft portion 22B and bringing "JIS" TECLOCK Durometer (manufactured by TECLOCK Corporation) into contact with the upper surfaces of these measurement pieces so that the measuring instrument may have the positional relationship of being perpendicular to the upper surfaces in a similar manner to that in the aforementioned embodiment.

According to such a configuration, when the pressing tool main body 10B is in an initial state, in which the pressing tool main body 10B is subject to no external force and is not squashed, the convex upper surface 11B has a hardness of from 10 to 20, which is a value of the International Rubber Hardness Degree (IRHD) complying with JIS Y 6253, and has a hardness of 11 in the present embodiment. In a case in which the hardness is less than 10, the pressing tool main body 10B has difficulty in giving a moderate pressing feeling to the occyx and the pubis of the human body at the time when the pressing tool main body 10B begins to press the pelvic floor muscle group. In a case in which the hardness exceeds 20, the pressing tool main body 10B gives a too strong pressing feeling to the coccyx and the pubis of the human body at the time when the pressing tool main body 10B begins to press the pelvic floor muscle group.

On the other hand, when the pressing tool main body 10B is subject to an external force, and the height from the seat surface to the convex upper surface, that is, the height from the convex lower surface 12B to the convex upper surface 11B, becomes a half of the height from the seat surface to the convex upper surface 11B in the initial state, the convex upper surface 11B has a hardness of 25 to 35, which is a value of the International Rubber Hardness Degree (ERIE)) complying with JIS K 6253, and has a hardness of 28 in the present embodiment. In a case in which the hardness is less than 25, the pressing tool main body 10B has difficulty in giving a moderate pressing feeling to the coccyx and the pubis of the human body at the time when the pressing tool main body 10B is fully pressing the pelvic floor muscle group. In a case in which the hardness exceeds 35, the pressing tool main body 10B gives a too strong pressing feeling to the coccyx and the pubis of the human body at the time when the pressing tool main body 10B is fully pressing the pelvic floor muscle group.

These hardness values are measured and obtained by bringing "JIS" TECLOCK Durometer (manufactured by TECLOCK Corporation) into contact with the part of the convex upper surface 11B corresponding to the center position of the pressing tool for a pelvic floor muscle group 1B in the front-back direction D2 and corresponding to the center position in the right-left direction D3 so that the measuring instrument may have the positional relationship of being perpendicular to the convex upper surface 11B in a similar manner to that in the aforementioned embodiment.

In a similar manner to that in the first embodiment, the pressing tool for a pelvic floor muscle group 1B having the pressing tool main body 10B configured as above is mounted on the seat surface S of a chair or the like, the human body H sits on the seat surface S and mounts the convex upper surface 11 of the pressing tool for a pelvic floor muscle group 1B to have a positional relationship in which the convex upper surface 11B is opposed to the pubis and the coccyx of the human body H, and the pressing tool for a pelvic floor muscle group 1B presses the pelvic floor muscle group. The pressing tool for a pelvic floor muscle group 1B is then deformed as illustrated in FIG. 6.

Here, the squashing amount of the pressing tool main body 10B at the part of the convex upper surface 11B opposed to the pubis in the direction approaching to the seat surface S, derived by the position of the convex upper surface 11B when the pressing tool main body 10B is squashed by the weight of the human body relative to the position of the convex upper surface 11B in the initial state, in which the pressing tool main body 10B is subject to no external force and is not squashed, is referred to as A, as illustrated in FIG. 6.

Also, the squashing amount of the pressing tool main body 10B at the part of the convex upper surface 11B opposed to the coccyx in the direction approaching to the seat surface S, derived by the position of the convex upper surface 11B when the pressing tool main body 10B is squashed by the weight of the human body relative to the position of the convex upper surface 11B in the initial state, in which the pressing tool main body 10B is subject to no external force and is not squashed, is referred to as B.

Furthermore, the squashing amount of the pressing tool main body 10B at the part of the convex upper surface 11B opposed to the pelvic floor muscle group between the pubis and the coccyx in the direction approaching the seat surface S, derived by the position of the convex upper surface 11B when the pressing tool main body 10B is squashed by the weight of the human body relative to the position of the convex upper surface 11B in the initial state, in which the pressing tool main body 10B is subject to no external force and is not squashed, is referred to as C.

At this time, relationships of $1.5 \leq A/C \leq 10$ and $1.4 \leq B/C \leq 9$ are established. In an example of the present embodiment, A is about 7 mm, B is about 6 mm, and C is about 3 mm. In a case in which A/C is less than 1.5, a pressing force of pressing the pelvic floor muscle group becomes a pressing force close to the pressing force with which the part of the convex upper surface 11B opposed to the pubis presses the pubis, and it is difficult to obtain the effect of tightening the pelvic floor muscle group by pressing the pubis moderately more strongly than the pressing force of pressing the pelvic floor muscle group. Also, in a case in which A/C exceeds 10, the pressing force of pressing the pelvic floor muscle group becomes much less weaker than the pressing force with which the part of the convex upper surface 11B opposed to the pubis presses the pubis, which makes it substantially difficult to press the pelvic floor muscle group.

Also, in a case in which B/C is less than 1.4, the pressing force of pressing the pelvic floor muscle group becomes a pressing force close to a pressing force with which the part of the convex upper surface 11B opposed to the coccyx presses the coccyx, and it is difficult to obtain the effect of tightening the pelvic floor muscle group by pressing the coccyx moderately more strongly than the pressing force of pressing the pelvic floor muscle group. Also, in a case in which B/C exceeds 9, the pressing force of pressing the pelvic floor muscle group becomes much less weaker than the pressing force with which the part of the convex upper surface 11B opposed to the coccyx presses the coccyx, which makes it substantially difficult to press the pelvic floor muscle group.

Next, a test was conducted to confirm the effect of the present invention by comparing the pressing tool for a pelvic floor muscle group 1B with products produced by changing the hardness, the shape, and the size of the hard portion and the soft portion, the position of the hard portion against the soft portion, and the like in the pressing tool main body 10B of the pressing tool for a pelvic floor muscle group 11B. In the test, the pressing tool for a pelvic floor muscle group 1B according to the third embodiment was called Invented Product 4. Also, pressing tools for the pelvic floor muscle group having the following pressing tool main bodies were called Invented Product 5 and Invented Product 6, respectively, and the pressing tools for the pelvic floor muscle group having the following pressing tool main bodies were called Comparative Product 5 and Comparative Product 6, respectively. Below, the hardness values are obtained by a similar measuring method to that for obtaining the hardness in the present embodiment.

Invented Product 5 is as follows. As for the pressing tool main body, the convex upper surface has a hardness of 12, which is a value of the International Rubber Hardness Degree (IRHD) complying with JIB K 6253, when the pressing tool main body is in the initial state, in which the pressing tool main body is subject to no external force and is not squashed, and has a hardness of 26, which is a value of the International Rubber Hardness Degree (IRHD) complying with JIS K 6253, when the pressing tool main body is subject to an external force, and the height from the seat, surface S to the convex upper surface becomes a half of the height from the seat surface S to the convex upper surface in the initial state. The hard portion and the soft portion have hardnesses of 21 and 5, respectively, which are values of the international Rubber Hardness Degree (IRHD) complying with JIS K 6253.

Invented Product 6 is as follows. As for the pressing tool main body, the convex upper surface has a hardness of 15, which is a value of the International Rubber Hardness Degree (IRHD) complying with JIS K 6253, when the pressing tool main body is in the initial state, in which the pressing tool main body is subject to no external force and is not squashed, and has a hardness of 31, which is a value of the International Rubber Hardness Degree (IRHD) complying with 315 K 6253, when the pressing tool main body is subject to an external force, and the height from the seat surface S to the convex upper surface becomes a half of the height from the seat surface to the convex upper surface in the initial state. The hard portion and the soft portion have hardnesses of 25 and 7, respectively, which are values of the International. Rubber Hardness Degree (IRHD) complying with JIS K 6253.

Comparative Product 5 is as follows. As for the pressing tool main body, the convex upper surface has a hardness of 4, which is a value of the International Rubber Hardness Degree (IRHD) complying with JIS K 6253, when the pressing tool main body is in the initial state, in which the pressing tool main body is subject to no external force and is not squashed, and has a hardness of 19, which is a value of the International Rubber Hardness Degree (IRHD) complying with JIS K 6253, when the pressing tool main body is subject to an external force, and the height from the seat surface S to the convex upper surface becomes a half of the height from the seat surface to the convex upper surface in the initial state. The hard portion and the soft portion have hardnesses of 17 and 3, respectively, which are values of the International Rubber Hardness Degree (IRHD) complying with JIS K 6253.

Comparative Product 6 is as follows. As for the pressing tool main body, the convex upper surface has a hardness of 14, which is a value of the International Rubber Hardness Degree (IRHD) complying with JIS K 6253, when the pressing tool main body is in the initial state, in which the pressing tool main body is subject to no external force and is not squashed, and has a hardness of 38, which is a value of the international Rubber Hardness Degree (IRHD) complying with JIS K 6253, when the pressing tool main body is subject to an external force, and the height from the seat surface S to the convex upper surface becomes a half of the height from the seat surface to the convex upper surface in the initial state. The hard portion and the soft portion have hardnesses of 25 and 14, respectively, which are values of the International Rubber Hardness Degree (IRHD) complying with JIS K 6253.

Fifty examinees used the pressing tools for the pelvic floor muscle group to examine whether or not each of them felt pain in the part around the pubis and the part around the coccyx and the degree of pressing on the pelvic floor muscle group. Specifically, the number of substantially unsatisfied examinees, who each felt that the degree of pressing on the pelvic floor muscle group was not bad but could be hither, out of the fifty examinees was counted as the number of "Unsatisfied" examinees. Also, the number of examinees who each felt that the degree of pressing on the pelvic floor muscle group was sufficient and comfortable and that he/she wanted to use it for a longer time out of the fifty examinees was counted as the number of "Satisfactory Pressing" examinees. Furthermore, the number of examinees who each felt that pressing was sufficient but who each felt strange after use out of the fifty examinees was counted as the number of "Strange Feeling" examinees. The test result is shown in Table 9 below.

TABLE 9

|  | Comparative Product 5 | Invented Product 4 | Invented Product 5 | Invented Product 6 | Comparative Product 6 |
| --- | --- | --- | --- | --- | --- |
| Unsatisfied | 47 People | 6 People | 2 People | 1 People | 0 People |
| Satisfactory Pressing | 3 People | 43 People | 46 People | 45 People | 9 People |
| Strange Feeling | 0 People | 1 People | 2 People | 4 People | 41 People |

As shown in Table 9, the number of examinees who felt unsatisfied or strange is small in the case of Invented Product 4, Invented Product 5, and Invented Product 6. Conversely, most of the examinees answered that they felt unsatisfied in the case of Comparative Product 5. Also, most of the examinees felt strange after using Comparative Product 6 and did not feel that they wanted to use Comparative Product 6 for a longer time.

The following is apparent from this result. That is, the soft portion has a hardness of 1 or higher and 10 or lower, which is a value of the International Rubber Hardness Degree (IRHD) complying with JIS K 6253, and the hard portion has a hardness of 20 or higher and 100 or lower, which is a value of the International Rubber Hardness Degree (IRHD) complying with JIS K 6253. As for the pressing tool main body, the convex upper surface has a hardness of 10 to 20, which is a value of the International Rubber Hardness Degree (IRHD) complying with JIS K 6253, when the pressing tool main body is in the initial state, in which the pressing tool main body is subject to no external force and is not squashed, and has a hardness of 25 to 35, which is a value of the International Rubber Hardness Degree (IRHD) complying with JIS K 6253, when the pressing tool main body is subject to an external force, and the height from the seat surface to the convex upper surface becomes a half of the height from the seat surface to the convex upper surface in the initial state. It is apparent that such Invented Products can be comfortable to use and can make users feel that they want to use them for a longer time.

Next, another test was conducted to confirm the effect of the present invention by comparing the pressing tool for a pelvic floor muscle group 1B with products produced by changing the hardness, the shape, and the size of the hard portion and the soft portion, the position of the hard portion against, the soft portion, and the like in the pressing tool main body 10B of the pressing tool for a pelvic floor muscle group 1B. In the test, the pressing tool for a pelvic floor muscle group 1B according to the third embodiment was called Invented Product 4. Also, pressing tools for the pelvic floor muscle group having the following pressing tool main bodies were called Invented Product 7 and Invented Product 8, respectively, and the pressing tools for the pelvic floor muscle group having the following pressing tool main bodies were called Comparative Product 7 and Comparative Product 8, respectively.

A product having the squashing amounts corresponding to A, B, and C in FIG. 6 of 5 mm, 4 mm, and 2 mm was called Invented Product 7. A product having the squashing amounts corresponding to A, B, and C in FIG. 6 of 8 mm, 7 mm, and 4 mm was called Invented Product 8. A product having the squashing amounts corresponding to A, B, and C in FIG. 6 of 4 mm, 4 mm, and 3 mm was called Comparative Product 7. A product having the squashing amounts corresponding to A, B, and C in FIG. 6 of 12 mm, 11 mm, and 1 mm was called Comparative Product 8.

Fifty examinees used the pressing tools for the pelvic floor muscle group to examine whether or not each of them felt pain in the part around the pubis and the part around the coccyx and the degree of pressing on the pelvic floor muscle group. Specifically, the number of substantially unsatisfied examinees who each felt that the degree of pressing on the pelvic floor muscle group was not had but could be higher out of the fifty examinees was counted as the number of "Unsatisfied" examinees. Also, the number of examinees who each felt that the degree of pressing on the pelvic floor muscle group was sufficient and comfortable and that he/she wanted to use it for a longer time out of the fifty examinees was counted as the number of "Satisfactory Pressing" examinees. Furthermore, the number of examinees who each felt that pressing was sufficient but who each felt strange after use out of the fifty examinees was counted as the number of "Strange Feeling" examinees. The test result is shown in Table 10 below.

TABLE 10

|  | Comparative Product 7 | Invented Product 4 | Invented Product 7 | Invented Product 8 | Comparative Product 8 |
| --- | --- | --- | --- | --- | --- |
| Unsatisfied | 8 People | 3 People | 1 People | 1 People | 11 People |
| Satisfactory Pressing | 1 People | 43 People | 46 People | 47 People | 3 People |
| Strange Feeling | 41 People | 4 People | 3 People | 2 People | 36 People |

As shown in Table 9, the number of examinees who felt unsatisfied or strange is small in the case of Invented Product 4, Invented Product 7, and Invented Product 8. Conversely, most of the examinees felt strange in the case of Comparative Product 7. Also, the examinees felt strange after use of Comparative Product 8 at a high rate and did not feel that they wanted to use Comparative Product 8 for a longer time. Also, many examinees felt unsatisfied in the case of Comparative Product 8.

It is apparent from this result that Invented Products can be moderately comfortable to use and can make users feel that they want to use them for a longer time when the value for A, the value for B, and the value for C in FIG. 6 have relationships of $1.5 \leq A/C \leq 10$ and $1.4 \leq B/C \leq 9$.

Next, a pressing tool for a pelvic floor muscle group 1C according to a fourth embodiment of the present invention will be described with reference to FIG. 7. The pressing tool for a pelvic floor muscle group 1C according to the fourth embodiment differs from the pressing tool for a pelvic floor muscle group 1B according to the third embodiment in that a hard portion 21C is located in a dispersed state. The other parts are equal to those of the pressing tool for a pelvic floor muscle group 1B according to the first embodiment, and a description thereof is thus omitted.

As illustrated in FIG. 7, multiple hard portions 21C are located in a soft portion 22C in a dispersed state. According to this configuration, the pressing tool for a pelvic floor muscle group 1C has hardness and squashing amount characteristics that are similar to those for the pressing tool for a pelvic floor muscle group 1B according to the third embodiment. It is to be noted that, in FIG. 7, the hard portions 21C are distributed around the center of the soft portion 22C for convenience of description, but actually, the hard portions 21C are distributed up to the position quite proximate to the outer surface of the soft portion 22C. In this manner, by dispersing the hard portions 21C in the soft portion 22C, the hardness and the squashing amount characteristics of the pressing tool for a pelvic floor muscle group 1C may be easily similar to those of the pressing tool for a pelvic floor muscle group 1B according to the third embodiment.

Next, a pressing tool for a pelvic floor muscle group 1D according to a fifth embodiment of the present invention will be described with reference to FIG. 8. The dimensions and the like of the pressing tool for a pelvic floor muscle group 1D according to the fifth embodiment partially differ from those of the pressing tool for a pelvic floor muscle group 1B according to the third embodiment. The other parts are equal to those of the pressing tool for a pelvic floor muscle group 1B according to the first embodiment, and a description thereof is thus omitted.

The convex upper surface 11D serving as the upper surface of the pressing tool for a pelvic floor muscle group 1D is formed approximately in a semicircular shape having a radius of 56.25 mm as seen from the front surface. Also, the convex lower surface 12D serving as the lower surface of the pressing tool for a pelvic floor muscle group 1 is formed in an arc having a radius of 80 mm as seen from the front surface as illustrated in FIG. 5. The distance from the upper end to the lower end of the pressing tool for a pelvic floor muscle group 1D, that is, the maximum distance between the convex upper surface 11D serving as the upper surface and the convex lower surface 12D serving as the lower surface, is preferably from 60 mm to 120 mm, and is 100 mm in the present embodiment. In a case in which the maximum distance is less than 60 mm, even when the pressing tool main body 103D has moderate elasticity, the maximum distance between the convex upper surface 11D and the convex lower surface 12D serving as the lower surface is too short for a well-built Westerner to press the pubis, the coccyx, and the pelvic floor muscle group sufficiently in the case in which the Westerner uses the pressing tool for a pelvic floor muscle group 1D. In a case in which the maximum distance exceeds 120 mm, the maximum distance between the convex upper surface 11D and the convex lower surface 12D serving as the lower surface is too long even for the well-built Westerner to press the pubis, the coccyx, and the pelvic floor muscle group moderately.

The length between a front end surface 15D and a back end surface 16D, that is, the length in the longitudinal direction of the pressing tool for a pelvic floor muscle group 1D, is preferably 300 mm or longer, and is 350 mm in the pressing tool for a pelvic floor muscle group 1D according to the second embodiment. In a case in which the length in the longitudinal direction of the pressing tool for a pelvic floor muscle group 1D is less than 300 mm, the front end surface 15D and the back end surface 16D of the pressing tool for a pelvic floor muscle group 1D are completely buried under a user who mounts the pressing tool for a pelvic floor muscle group 1D, and it is difficult to confirm whether or not the pressing tool for a pelvic floor muscle group 1D is located at the appropriate position relative to the pubis and the coccyx of the user in the case in which the user of the pressing tool for a pelvic floor muscle group 1D is a well-built Westerner. A 207 mm part on one end side (left side in FIG. 8) out of the 350 mm length constitutes the pressing tool main body 103D. A 143 mm part on the other end side (right side in FIG. 8) constitutes a pressing tool main body position confirming portion 104D formed integrally with and connected with the end of the pressing tool main body 103D in the longitudinal direction of the pressing tool main body.

As described above, the pressing tool for a pelvic floor muscle group 1D includes the pressing tool main body position confirming portion 104D connected with the end of the pressing tool main body 103D in the longitudinal direction of the pressing tool main body 103D. The entire length of the pressing tool for a pelvic floor muscle group 1D including the pressing tool main body 103D and the pressing tool main body position confirming portion 104D in the longitudinal direction of the pressing tool main body 103D is 350 mm, which is within the range of 300 mm or longer. This configuration can prevent the pressing tool for a pelvic floor muscle group 1D from being completely buried under the groin and the buttocks due to a large physique when the Westerner uses the pressing tool for a pelvic floor muscle group 1D. As a result, another person such as a training coach can visually recognize the pressing tool main body position confirming portion 104D and can easily confirm whether or not the pressing tool main body 103D is located at an appropriate position relative to the pubis, the coccyx, and the pelvic floor muscle group.

Also, since the pressing tool for a pelvic floor muscle group 1D includes the convex lower surface 12D serving as the lower surface having the positional relationship of being opposed to the convex upper surface 11D, and the maximum distance between the convex upper surface 11D and the convex lower surface 12D serving as the lower surface is 100 mm, which is within the range of 60 mm to 120 mm, it is possible to restrict insufficient pressing on the part of the pubis, the part of the coccyx, and the pelvic floor muscle group caused by racial differences concerning the size of a pelvic diaphragm, the amounts of fat and collagen, the thickness of a vulva around a vagina, and the like when a Westerner uses the pressing tool for a pelvic floor muscle group 1D.

The present invention is not limited to the aforementioned embodiments and can be modified within the technical scope described in the patent claims. For example, the shape of the pressing tool for a pelvic floor muscle group is not limited to those of the pressing tools for a pelvic floor muscle group 1 and 1A according to the present embodiments. For example, the pressing tool for a pelvic floor muscle group has only to have a length at least as long as the length between the pubis and the coccyx of the human body H in the longitudinal direction and have a width shorter than the length between the ischia, as a pair, of the human body H in the width direction with respect to the longitudinal direction. The entire part of the pressing tool for a pelvic floor muscle group in the longitudinal direction corresponding to the length between the pubis and the coccyx of the human body H has only to have the convex upper surface curved outward from one end to the other end of the with respect to the longitudinal direction. Also, the shape of the convex upper surface is not limited, to the curved shape. Similarly, the shape of the surface on the side of the lower direction D12 opposed to the convex upper surface is not limited to being a flat or convex lower surface according to the present embodiments.

Also, each of the pressing tools for the pelvic floor muscle group 1 and 1A according to the present embodiments may not necessarily be made of urethane resin but of a single material other than urethane resin. The pressing tool for a pelvic floor muscle group 1 has only to have a distance from the upper end to the lower end of 30 mm to 60 mm and have a hardness of 10 to 20. Furthermore, the material for each of the pressing tools for the pelvic floor muscle group 1 and 1A according to the present embodiments is not limited to a single material, such as urethane resin. For example, each of the pressing tools for the pelvic floor muscle group 1 and 1A may be made of two materials consisting of a core material and a surrounding material surrounding the core material. In this case, a urethane resin may be used as the core material while a material having a lower degree of hardness than the urethane resin may be used as the surrounding material. Conversely, a urethane resin may be used as the surrounding material while a material having a lower degree of hardness than the urethane resin may be used as the surrounding material. In this case as well, a resin other than urethane resin may be used. Furthermore, the core material may be made of two or more materials. In this case as well, the pressing tool for a pelvic floor muscle group 1 has only to have a distance from the upper end to the lower end of 30 mm to 60 mm and have a hardness of 10 to 20.

Furthermore, although each of the pressing tools for the pelvic floor muscle group 1 and 1A according to the present embodiments is formed integrally in a bar shape, it may be formed to be vertically separable with a plane parallel to the seat surface serving as a cutting plane, for example. In this case, it is desirable to keep the respective members that have been vertically separated in an integrated state by appropriately being convexo-concave on the cutting plane of the respective members so as to prevent the respective members from being inadvertently separated. Also, a plurality of cutting planes may be provided to make each pressing tool separable into three or more members.

By providing the plurality of cutting planes and combining one or a plurality of separated members, the distance from the upper end to the lower end of the pressing tool for a pelvic floor muscle group 1 in the up-down direction D1 may be adjusted finely within the range of 30 mm to 60 mm, for example. Also, the respective separated members may be made of materials different from each other. For example, the upper member may be made of a urethane resin while the other members may be made of other materials.

Also, a sacrum opposing mark may be provided for aligning the pressing tool for a pelvic floor muscle group with the sacrum of the human body.

Also, although the pressing tool main body includes a hard portion and a soft portion in the third to fifth embodiments, the present invention is not limited to this configuration. For example, by arbitrarily selecting an appropriate material so that the pressing tool main body may have a similar characteristic of hardness to those in the third to fifth embodiments even in a case in which the pressing tool main body is made of a uniform material as in the first and second embodiments, the pressing tool main body may be made of a uniform material. Also, the material for the pressing tool main body is not limited to a urethane resin. For example, the pressing tool main body may be made of a metal or the like.

EXPLANATION OF REFERENCE NUMERALS 1, 1A, 1B, 1C, 1D Pressing tool for a pelvic floor muscle group 10, 10A, 10B, 10C, 103D Pressing tool main body
11, 11A, 11B, 11C Convex upper surface
12, 12B, 12C Convex lower surface
12A Lower surface
101, 101A Left end of the pressing tool for a pelvic floor muscle group
102, 102A Right end of the pressing tool for a pelvic floor muscle group
D2 Front-back direction
H Human body
S Seat surface

The invention claimed is:

1. A pressing tool adapted for use with a pelvic floor muscle group of a human body comprising:
a pressing tool main body having a length in a longitudinal direction adapted to be at least as long as a length between a pubis and a coccyx and having a width in a width direction with respect to the longitudinal direction that is adapted to be shorter than a length between an ischia, as a pair,
wherein a part of the pressing tool main body in the longitudinal direction is configured to be at least as long as the length between the pubis and the coccyx has a convex upper surface formed in a convex shape headed outward from the pressing tool main body,
wherein a convex lower surface is provided at a position opposed to the convex upper surface and the convex lower surface is formed in an arc having a curvature larger than the convex upper surface,
wherein the pressing tool for a pelvic floor muscle group is mounted to have a positional relationship in which the longitudinal direction corresponds to a front-back direction so that the convex upper surface may be located highest in the pressing tool main body and so that the longitudinal direction of the pressing tool main body may be along a seat surface, and the pressing tool is configured such that when the human body sits on the seat surface and mounts the convex upper surface, the convex upper surface is adapted to oppose the pubis and the coccyx,
wherein, as for the pressing tool main body, the convex upper surface has a hardness of 10 to 20, which is a value of the International Rubber Hardness Degree (IRHD) complying with JIS K 6253, when the pressing tool main body is in an initial state in which the pressing tool main body is subject to no external force and is not squashed, and has a hardness of 25 to 35, which is a value of the International Rubber Hardness Degree (IRHD) complying with JIS K 6253, when the pressing tool main body is subject to being squashed during use, and a height from the seat surface to the convex upper surface becomes a half of the height from the seat surface to the convex upper surface in the initial state, and
wherein the pressing tool main body has a hard portion made of a urethane resin and a soft portion made of a urethane resin.

2. The pressing tool according to claim 1 further comprising a pressing tool main body position confirming portion connected with an end of the pressing tool main body in the longitudinal direction of the pressing tool main body.

3. The pressing tool according to claim 2, wherein an entire length of the pressing tool for a pelvic floor muscle group including the pressing tool main body and the pressing tool main body position confirming portion in the longitudinal direction of the pressing tool main body is between 300 mm and 350 mm.

4. The pressing tool according to claim 1, wherein a maximum distance between the convex upper surface and a lower surface is 60 mm to 120 mm.

5. The pressing tool according to claim 1, wherein the hard portion comprises a plurality of hard portions separately dispersed in the soft portion.

6. A pressing tool adapted for use for a pelvic floor muscle group of a human body comprising:
a pressing tool main body having a length in a longitudinal direction adapted to be at least as long as a length between a pubis and a coccyx of a human body and having a width in a width direction with respect to the longitudinal direction that is adapted to be shorter than a length between an ischia, as a pair, of the human body,
wherein a part of the pressing tool main body in the longitudinal direction is configured to be at least as long as the length between the pubis and the coccyx of the human body has a convex upper surface formed in a convex shape headed outward from the pressing tool main body,
wherein a convex lower surface is provided at a position opposed to the convex upper surface and the convex lower surface is formed in an arc having a curvature larger than the convex upper surface,
wherein the pressing tool for a pelvic floor muscle group is adapted to be mounted to have a positional relationship in which the longitudinal direction corresponds to a front-back direction of the human body so that the convex upper surface may be located highest in the pressing tool main body and so that the longitudinal direction of the pressing tool main body may be along a seat surface, and the pressing tool is configured such that when the human body sits on the seat surface and mounts the convex upper surface, the convex upper surface is adapted to oppose the pubis and the coccyx,
wherein a squashing amount of the pressing tool main body at a part of the convex upper surface configured to be opposed to the pubis in a direction approaching to the seat surface, derived by a position of the convex upper surface when the pressing tool main body is squashed relative to a position of the convex upper surface in an initial state in which the pressing tool main body is subject to no external force and is not squashed is referred to as "A",
wherein a squashing amount of the pressing tool main body at a part of the convex upper surface configured to be opposed to the coccyx in the direction approaching to the seat surface and configured to be squashed, derived by a position of the convex upper surface when the pressing tool main body is squashed relative to a position of the convex upper surface in the initial state in which the pressing tool main body is subject to no external force and is not squashed is referred to as "B",
wherein a squashing amount of the pressing tool main body at a part of the convex upper surface opposed to the pelvic floor muscle group between the pubis and the coccyx in the direction approaching to the seat surface, derived by a position of the convex upper surface when the pressing tool main body is squashed relative to a position of the convex upper surface in the initial state in which the pressing tool main body is subject to no external force and is not squashed is referred to as "C", and wherein, at this time, $1.5 \leq "A"/"C" \leq 10$ and $1.4 \leq "B"/"C" \leq 9$ are established, and
wherein the pressing tool main body has a hard portion made of a urethane resin and a soft portion made of a urethane resin.

7. The pressing tool according to claim 6, further comprising a pressing tool main body position confirming portion connected with an end of the pressing tool main body in the longitudinal direction of the pressing tool main body.

8. The pressing tool according to claim 6, wherein a maximum distance between the convex upper surface and a lower surface is 60 mm to 120 mm.

9. A pressing tool adapted for use with a pelvic floor muscle group of human body comprising:
- a pressing tool main body having a length in a longitudinal direction adapted to be at least as long as a length between a pubis and a coccyx and having a width in a width direction with respect to the longitudinal direction that is adapted to be shorter than a length between an ischia, as a pair,
- wherein a part of the pressing tool main body in the longitudinal direction is configured to be at least as long as the length between the pubis and the coccyx has a convex upper surface formed in a convex shape headed outward from the pressing tool main body,
- wherein a convex lower surface is provided at a position opposed to the convex upper surface and the convex lower surface is formed in an arc having a curvature larger than the convex upper surface,
- wherein the pressing tool for a pelvic floor muscle group is mounted to have a positional relationship in which the longitudinal direction corresponds to a front-back direction so that the convex upper surface may be located highest in the pressing tool main body and so that the longitudinal direction of the pressing tool main body may be along a seat surface, and the pressing tool is configured such that when the human body sits on the seat surface and mounts the convex upper surface, the convex upper surface is adapted to oppose the pubis and the coccyx, and
- wherein the pressing tool main body has a hard portion made of a urethane resin and a soft portion made of a urethane resin; and wherein the soft portion has a hardness of 1 or higher and 10 or lower, which is a value of the International Rubber Hardness Degree (IRHD) complying with JIS K 6253; and wherein the hard portion has a hardness of 20 or higher and 100 or lower, which is a value of the International Rubber Hardness Degree (IRHD) complying with JIS K 6253.

10. The pressing tool according to claim 9, further comprising a pressing tool main body position confirming portion connected with an end of the pressing tool main body in the longitudinal direction of the pressing tool main body.

11. The pressing tool according to claim 9, wherein a maximum distance between the convex upper surface and the lower surface is 60 mm to 120 mm.

* * * * *